US006800075B2

United States Patent
Mische et al.

(10) Patent No.: US 6,800,075 B2
(45) Date of Patent: Oct. 5, 2004

(54) METHOD TO INJECT AND EXTRACT FLUID AT A TREATMENT SITE TO REMOVE DEBRIS

(75) Inventors: Hans Mische, St. Cloud, MN (US); Robert C. Beck, St. Paul, MN (US)

(73) Assignee: Sprite Solutions, St. Paul, MN (US)

( * ) Notice: Subject to any disclaimer, the term of this patent is extended or adjusted under 35 U.S.C. 154(b) by 0 days.

(21) Appl. No.: 10/231,507

(22) Filed: Aug. 30, 2002

(65) Prior Publication Data

US 2003/0073953 A1 Apr. 17, 2003

Related U.S. Application Data

(63) Continuation-in-part of application No. 10/145,699, filed on May 16, 2002, and a continuation-in-part of application No. 10/050,978, filed on Jan. 18, 2002, and a continuation-in-part of application No. 09/995,303, filed on Nov. 27, 2001, and a continuation-in-part of application No. 09/637,529, filed on Aug. 11, 2000, and a continuation-in-part of application No. 09/459,225, filed on Dec. 10, 1999, now abandoned.

(60) Provisional application No. 60/402,680, filed on Aug. 12, 2002, and provisional application No. 60/316,122, filed on Aug. 30, 2001.

(51) Int. Cl.$^7$ ........................ A61M 29/00; A61M 31/00
(52) U.S. Cl. .................................... 604/509; 604/96.01
(58) Field of Search .......................... 604/22, 508, 509, 604/96.01, 102.01, 102.03, 102.02, 103.05, 152, 507; 606/194

(56) References Cited

U.S. PATENT DOCUMENTS

| | | | | |
|---|---|---|---|---|
| 5,135,482 A | * | 8/1992 | Neracher | ...................... 604/22 |
| 5,250,060 A | * | 10/1993 | Carbo et al. | ........... 604/164.13 |
| 5,462,529 A | * | 10/1995 | Simpson et al. | ....... 604/101.04 |

* cited by examiner

*Primary Examiner*—Loan H. Thanh
*Assistant Examiner*—Matthew DeSanto
(74) *Attorney, Agent, or Firm*—Beck & Tysver, P.L.L.C.

(57) ABSTRACT

A method and device for injecting and extracting fluid at a treatment site to remove debris from the site.

1 Claim, 7 Drawing Sheets

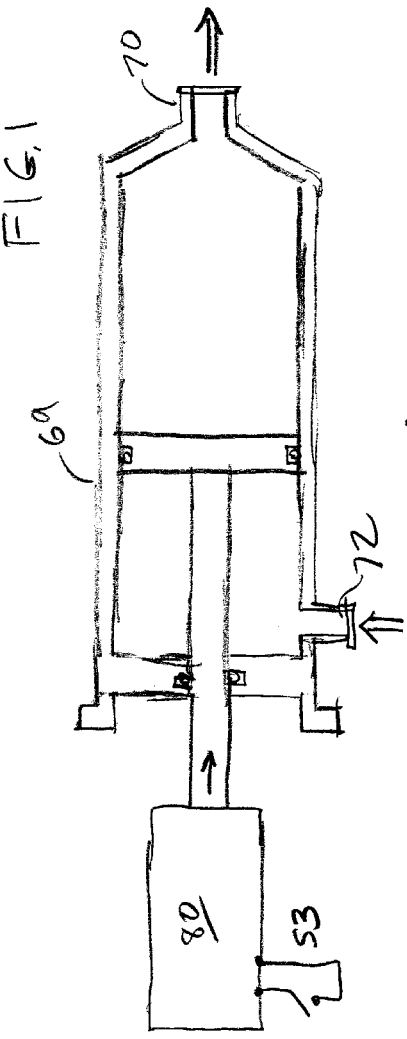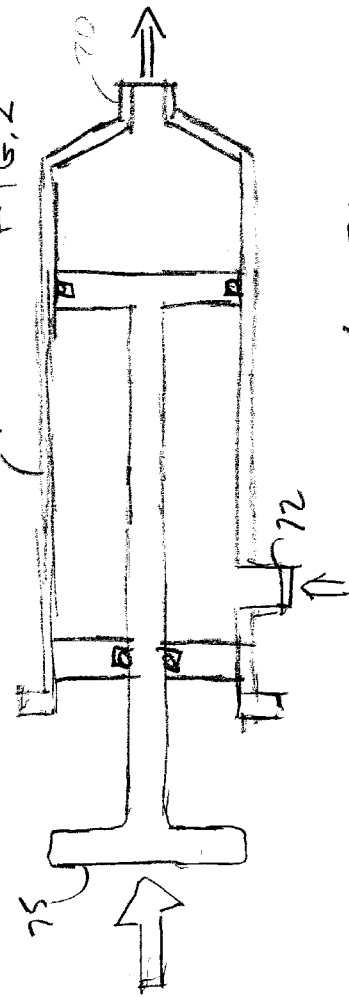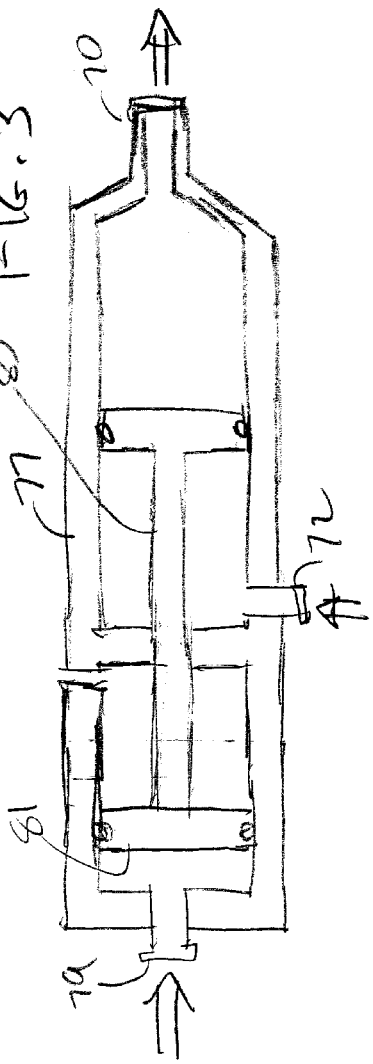

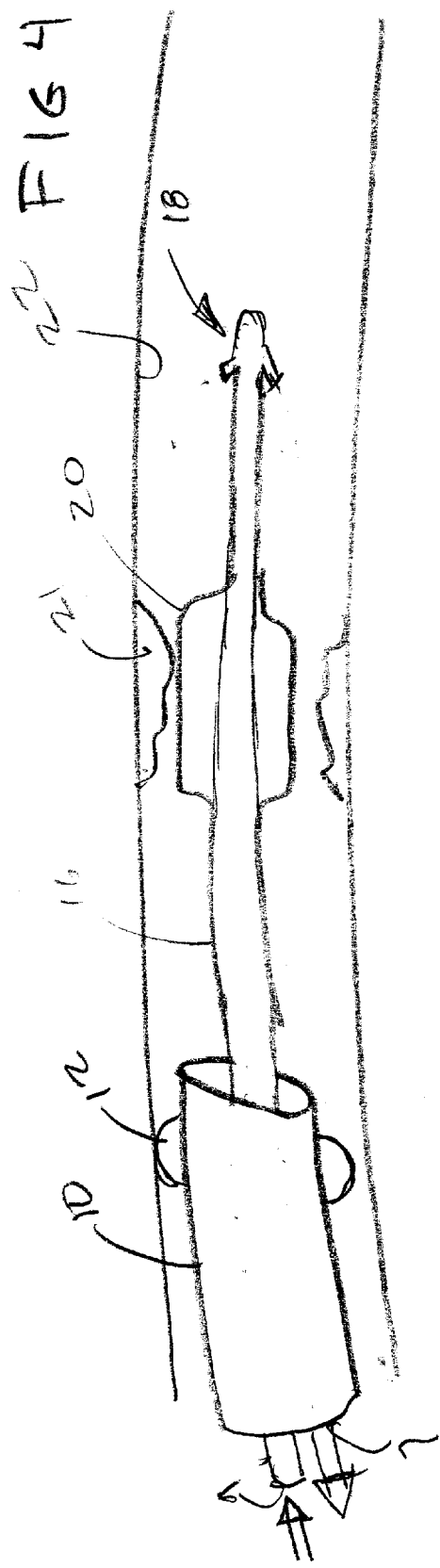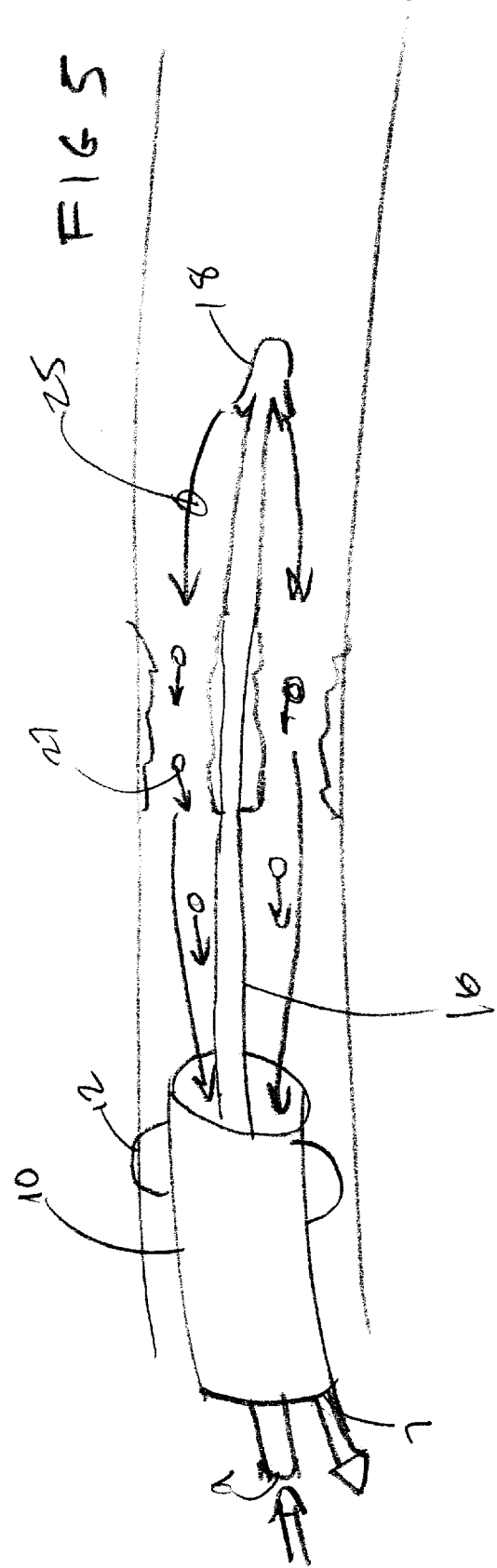

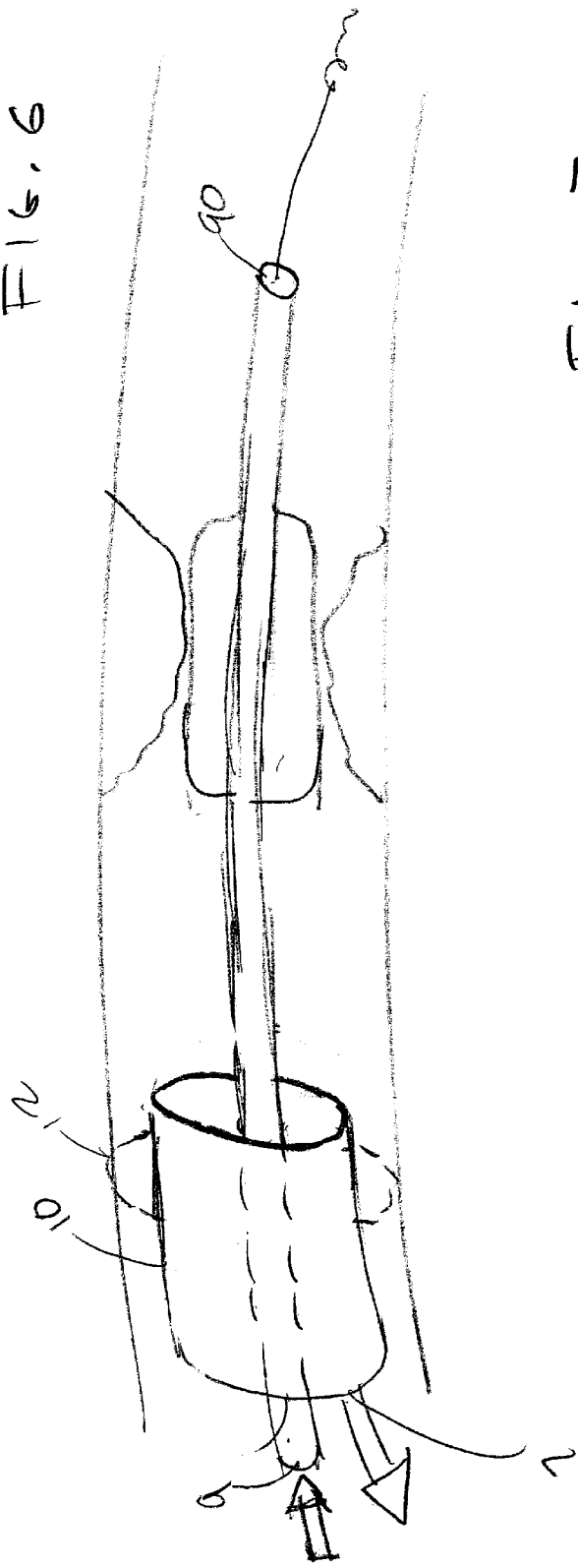
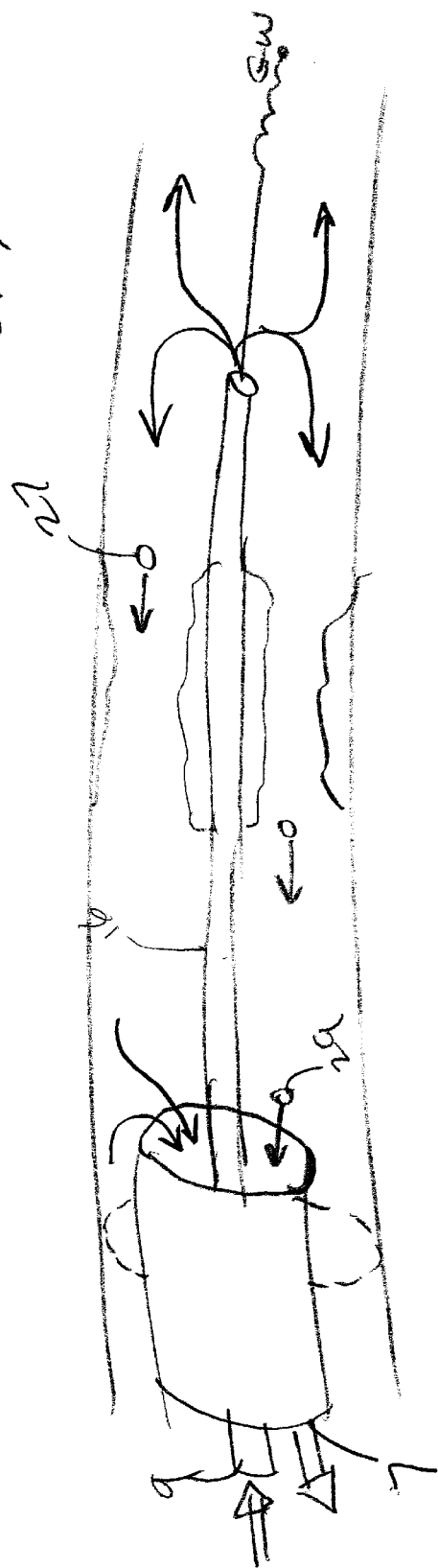

METHOD TO INJECT AND EXTRACT FLUID AT A TREATMENT SITE TO REMOVE DEBRIS

CROSS REFERENCE

This application is a utility case based upon provisional applications U.S. 60/402680 filed Aug. 12, 2002 and U.S. 60/316122 filed Aug. 30, 2001 each is incorporated by reference herein in their entirety.

The application is a CIP of U.S. Ser. No. 09/637,529 filed Aug. 11, 2000; U.S. Ser. No. 09/459,225 filed Dec. 10, 1999 now abandoned; U.S. Ser. No. 09/995,303 filed Nov. 27, 2001; U.S. Ser. No. 10/050,978 filed Jan. 18, 2002; U.S. Ser. No. 10/145,699 filed May 16, 2002. Each is incorporated by reference herein in their entirety.

FIELD OF THE INVENTION

The present invention relates to cardiology and more particularly to devices and methods for removing debris from vessels.

BRIEF DESCRIPTION OF THE DRAWINGS

Throughout the figures like reference numerals indicate equivalent structure wherein:

FIG. 1 is a schematic of the invention;
FIG. 2 is a schematic of the invention;
FIG. 3 is a schematic of the invention;
FIG. 4 is a schematic of the invention;
FIG. 5 is a schematic of the invention;
FIG. 6 is a schematic of the invention;
FIG. 7 is a schematic of the invention.

DETAILED DESCRIPTION

Figure 8:
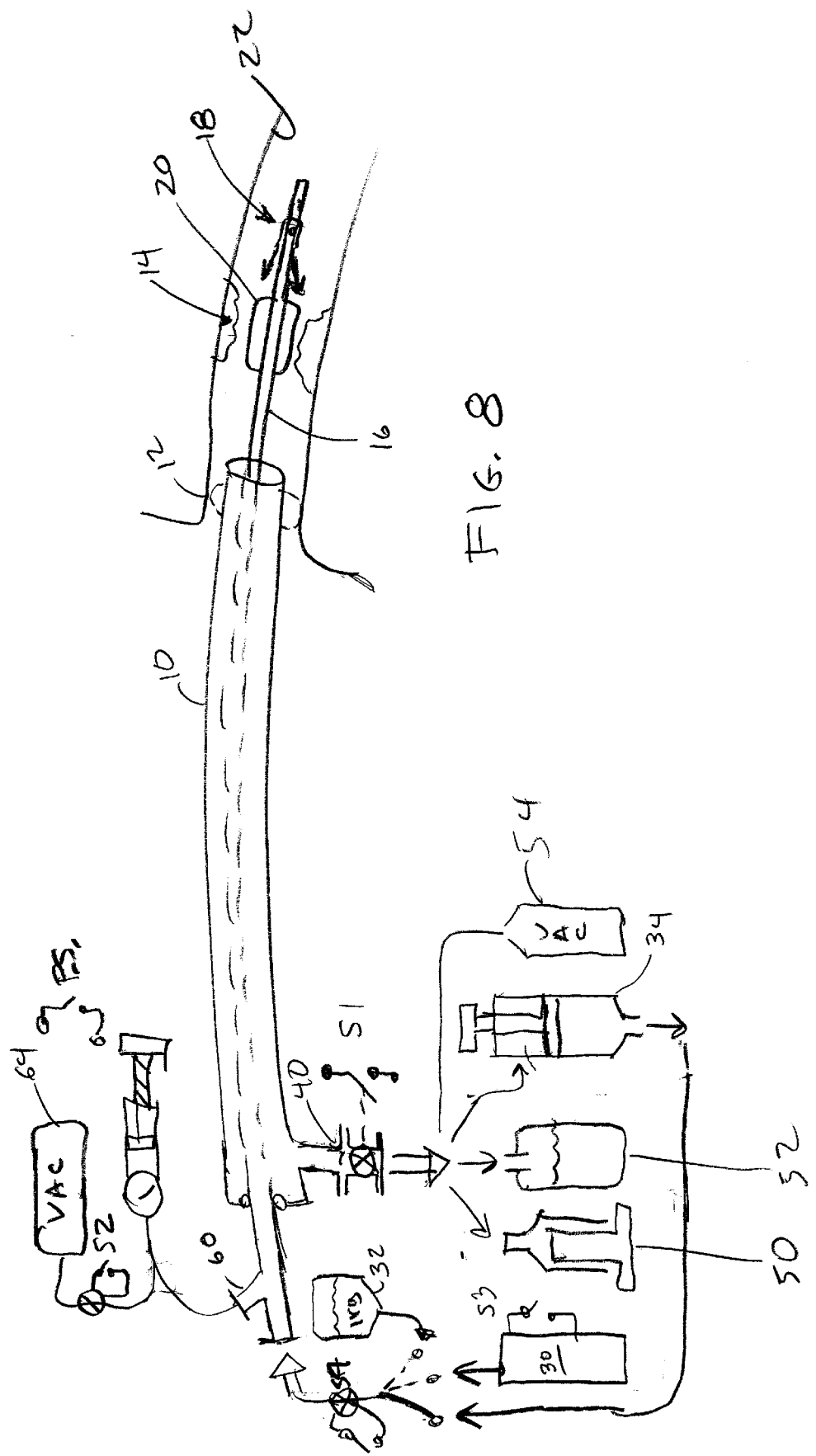
FIG. 8 is a schematic of the invention.

FIG. 8 shows the overall schematic of the treatment system. A guide sheath 10 with an optional occlusion balloon 12 is navigated to the treatment site 14. A balloon catheter 16 with a distal fluid delivery port 18 or nozzle is passed trough the guide catheter 10 to the treatment site.

Fluid injected into the catheter 16 emerges from the catheter distal of the balloon 20 and induces a retrograde flow in the vessel 22.

The injected fluid may be saline drugs or contrast agent or any biocompatible fluid. The source of fluid is selected from a conventional power injector 30 an irrigation bag suspended above the patient 32, a conventional syringe or a Gemini syringe 34.

The guide sheath is used to extract debris from the treatment site. The outflow passes trough a valve 40, which is associated with a switch S1. Preferably the valve 40 is actuated by closing S1 and/or the manual actuation of the valve sets the switch S1 to logic 1. The fluid drawn from the treatment site may be collected in a manual syringe 50 the low pressure side of Gemini 34 or a vacuum container 54 or a gravity fed collection bag 52.

The balloon inflation port 60 is coupled to inflation syringe 62 and a deflation vacuum reservoir 64 through a switch valve S2. Inflation of the balloon proceeds normally but deflation is preferably performed in synchrony with the heart. The physician activates the physician switch PS when he wants to deflate the balloon 20. Through logic, the valve S2 is opened and the balloon quickly deflated at an appropriate point in the cardiac cycle.

The catheter is freely movable within the sheath 10 both before during and after the procedure. That is the nozzle 18 can be "on" while the catheter is moving relative to the sheath.

FIG. 1 shows a Gemini dual syringe 69 with an injection outlet 70 and an extraction or recovery inlet 72. In this version of the device, it is attached to power injector 80, which maybe turned on, by the switch S3. The plunger 74 sweeps out a volume and the displaced fluid is injected out of the port 70. Recovered fluid from the sheath is collected at port 72. In this fashion the volume injected and extracted are directly coupled.

FIG. 2 shows a manually operated Gemini dual syringe 73 with a hand plunger 75. This version is useful for interventions where manual control of injection is desired.

FIG. 3 shows a "universal" Gemini dual syringe 77 where an additional injection ports 79 and power piston 81 drive a plunger 83. The power inlet port 79 may couple to pump or power injector to control injection.

FIG. 4 and FIG. 5 should be considered together as depicting a method of removing debris from a vessel. In FIG. 4, the balloon is inflated to treat the lesion 21 in vessel 22. A fluid injection lumen 9 in the catheter terminates in a retrograde flow-inducing nozzle 18. At the conclusion of the intervention, the balloon is quickly deflated while fluid is injected with nozzle 18. The retrograde flow depicted by arrow 25 sweeps debris indicated by particle 27 into the open mouth of the guide catheter 10. It is preferred to synchronize the balloon deflation with the fluid injection at a time when the flow in the guide catheter is at a maximum and coronary flow is at a minimum. This flow in the sheath 10 out the lumen 7 is propelled by either the low pressure side of a Gemini syringe 72 or a manual syringe or a vacuum container 54 or a gravity fed bag relying on aortic pressure to force flow in the sheath 10 lumen.

In the method of FIG. 4 and FIG. 5 The occlusion of the vessel 22 with an occlusion balloon 12 is optional and used if the flow in the guide sheath lumen 7 is too low to collect all the injected fluid and debris.

FIG. 6 an FIG. 7 show an alternate debris collection concept where fluid is injected through a guide wire lumen 90 without attempting to induce a retrograde flow. It should be appreciated that a dedicated fluid injection lumen may be used as an alternative. In FIG. 6 an intervention takes place normally and in FIG. 7 a large amount of fluid is injected into the vessel distal of the lesion to displace debris toward the open mouth of the guide sheath 10. Particles such as 27 and particle 29 are forced into the guide sheath where they are evacuated. If the flow rate of the guide sheath exceeds the injected fluid flow rate then the debris will all be sucked out without the use of an optional occlusion balloon 12.

Figure 12:
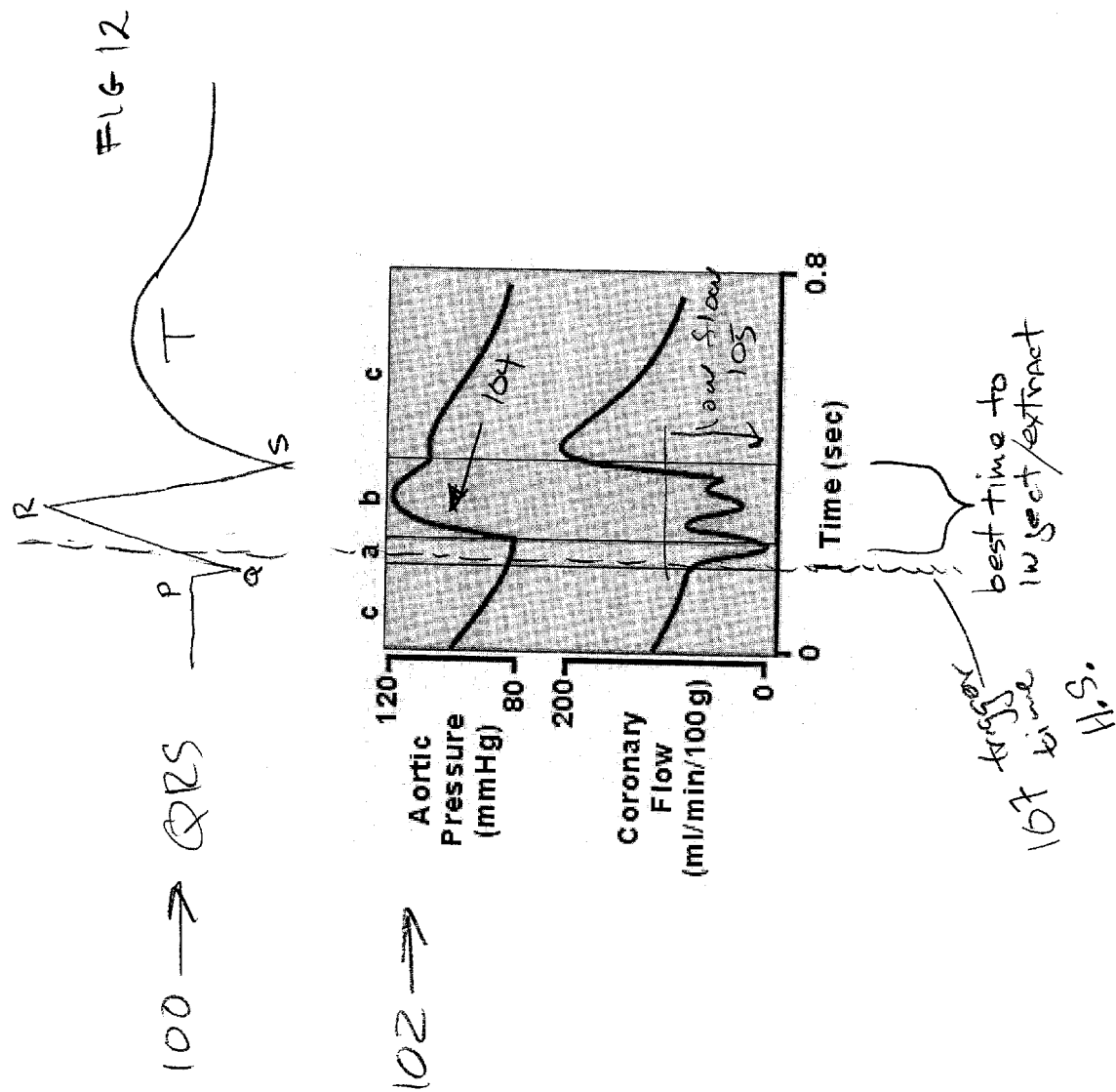
FIG. 12 is a schematic of the invention; and,
FIG. 13 is a schematic of the invention.

FIG. 12 shows a QRS electrocardiograph tracing of the heart over a chart showing the time course of pressure in the aorta and flow in the coronary vessels. The optimal time to inject fluid into the coronary vessel may be when the flow in the vessels is very low 105 due to ventricular contraction. At the isovolumeic, time the aortic pressure is rising very fast 104 and this helps to promote vigorous flow in the guide sheath lumen 7 out of the body.

Figure 11:
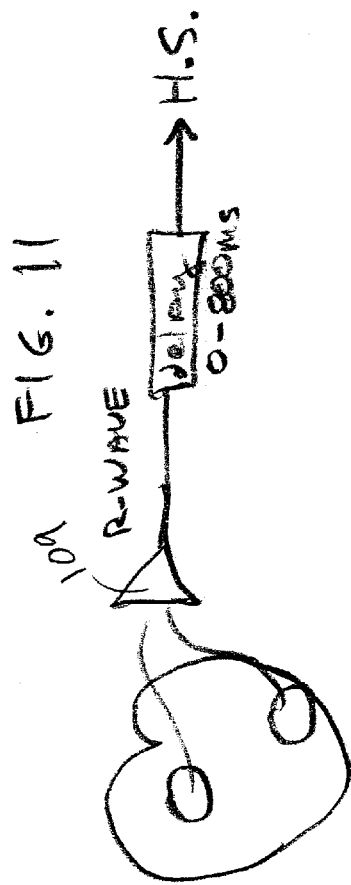
FIG. 11 is a schematic of the invention.

FIG. 11 shows a system to create the trigger time signal depicted as 107 in FIG. 12. Conventional surface electrodes over the heart sense the cardiac depolarization and are amplified in a sense amplifier 109 this signal triggers a delay timer which may delay the activation of the remaining circuits for a few milliseconds. Depending on the overall architecture of the system any one of several approaches to controlling the system may be taken.

Figure 9:
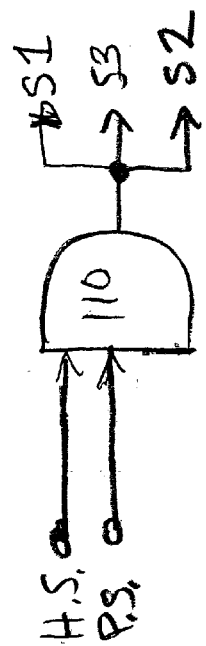
FIG. 9 is a schematic of the invention.

For example FIG. 9 assumes that a catheter structure taught by FIGS. 6 and 7 is set up with for example a conventional injector 30 coupled to the inlet 9 and a vacuum contain attached to the outlet port 40. In this instance, the physician signals his desire to deflate the balloon by activating the physician switch P.S. This is ANDED with the next R0-wave signal processed to give the heart signal H.S. With the and condition satisfied the logic 110 drives the switches S! which opens the sheath lumen 7 to the collection vessel. Essentially simultaneously, the balloon 20 is deflated by valve S2. At essentially the same time, the injector 30 is turned on by switch S3. Under these conditions, the particles 27 are displaced toward the lumen 7 by the volume of injected fluid at 9. Of course both anntegrade flow and retrograde flow occur with the simple fluid injection but the injected volume is set to exceed the ability of the vascular bed to accept the fluid forcing particulate retrograde into the waiting lumen 7.

Figure 10:
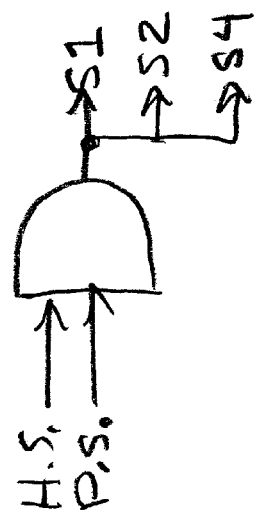
FIG. 10 is a schematic of the invention.

In FIG. 10 a different architecture may be employed for example a manual syringe may be connected as a fluid source for injection 9 and a collection bag 52. In this instance the physician signal to deflate is ANDED with the heart signal H.S. and the deflation switch S2 quickly deflates the balloon 20 while the closure of S4 allows fluid from the syringe to enter the vessel 22 through guidewire lumen in catheter 16. The opening of valve 40 by the closure of switch S1 allows the collected debris and blood and injectate to flow out of the system. Once these processes are started they may terminate within one heartbeat or they may continue over several beats. In general, the closure of the fluid injection process with precedes the closure of the sheath valve 40.

Figure 13:
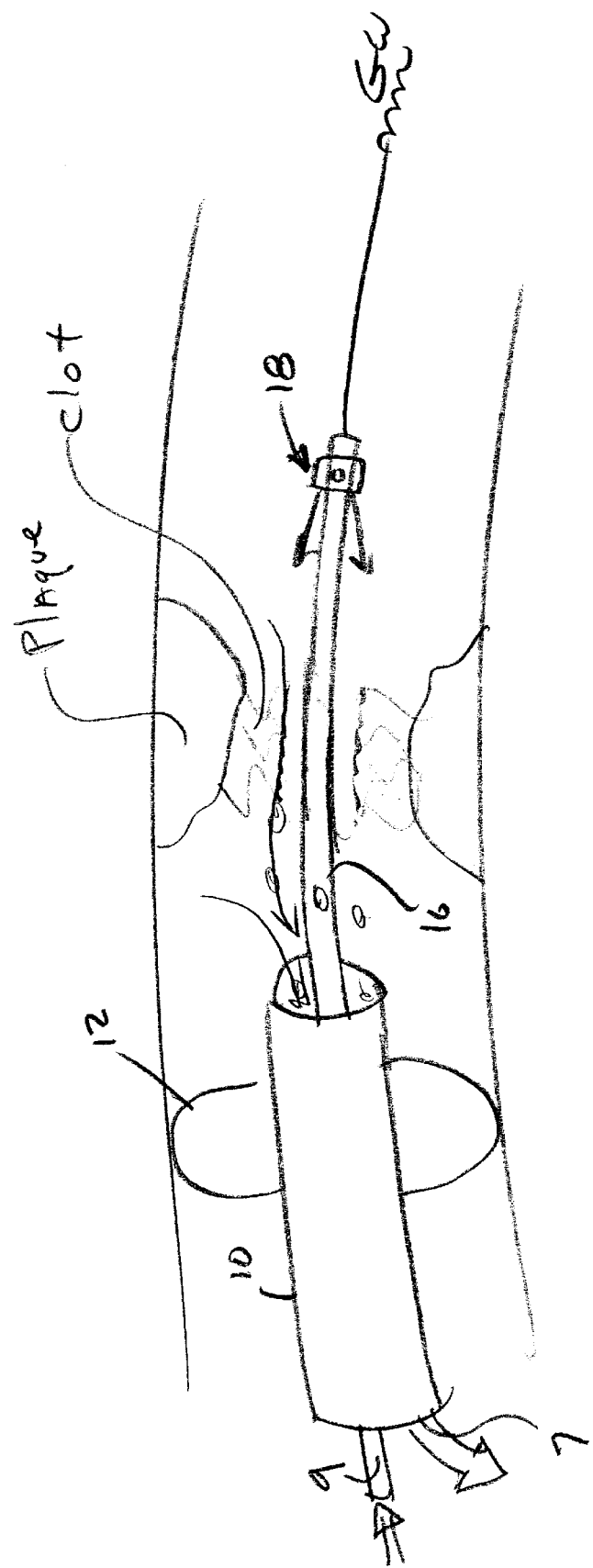

FIG. 13 shows a simplified system for treating acute myocardial infarction. In these cases, the vessel is occluded by a plaque lesion, which is blocked by a clot. By pushing a catheter with a retrograde induction, nozzel 18 on it through the clot the clot is cleared and the clot debris may be collected by the sheath lumen. Again, the occlusion balloon 12 on the sheath 10 is optional. When used it is inflated just before the clot is crossed and is deflated as the nozzle 18 is retracted into the sheath 10. Once again any fluid source and any collection vessel as depicted in FIG. 8 may be used with this embodiment.

It must be recognized that various combinations of injectors and extractors as set forth in FIG. 8 may be arranged to carry out the invention.

What is claimed is:

1. A method of removing debris from a treatment site in a vessel comprising the steps of:

occluding the vessel near a treatment site by inflating an occlusions balloon located on a delivery sheath of the type having an open lumen, said sheath located proximal of but near the therapy site; said vessel not being occluded distal of said therapy site by any medical device;

inflating a therapy balloon located on a therapy catheter at the treatment site to provide a therapy, said therapy creating debris, said therapy catheter being capable of independent motion with respect to said delivery sheath;

deflating said therapy balloon located on a therapy catheter at the treatment site, thereby releasing said debris;

injecting fluid into the therapy site through at least one port in said therapy catheter at a location distal of the therapy site at a rate and quantity sufficient to displace the debris into said delivery sheath lumen.

* * * * *